United States Patent [19]
Kohayakawa

[11] Patent Number: 5,483,305
[45] Date of Patent: Jan. 9, 1996

[54] EYE EXAMINING APPARATUS

[75] Inventor: Yoshimi Kohayakawa, Yokohama, Japan

[73] Assignee: Canon Kabushiki Kaisha, Tokyo, Japan

[21] Appl. No.: 184,046

[22] Filed: Jan. 21, 1994

[30] Foreign Application Priority Data

Jan. 25, 1993 [JP] Japan ................................ 5-029873
Apr. 21, 1993 [JP] Japan ................................ 5-117795

[51] Int. Cl.⁶ .................................................. A61B 3/02
[52] U.S. Cl. ........................ 351/243; 351/237; 351/239
[58] Field of Search .................... 351/243, 237, 351/239, 222, 211, 221

[56] References Cited

U.S. PATENT DOCUMENTS

| | | | |
|---|---|---|---|
| 4,155,632 | 5/1979 | Wolbarsht | 351/243 |
| 4,408,846 | 10/1983 | Balliet | 351/237 |
| 4,697,895 | 10/1987 | Sekiguchi et al. | 351/243 |
| 4,704,012 | 11/1987 | Kohayakawa et al. | 350/516 |
| 4,820,037 | 4/1989 | Kohayakawa et al. | 351/211 |
| 5,231,430 | 7/1993 | Kohayakawa | 351/243 |
| 5,237,351 | 8/1993 | Kohayakawa et al. | 351/243 |

FOREIGN PATENT DOCUMENTS 61-255634  11/1986  Japan.

*Primary Examiner*—William L. Sikes
*Assistant Examiner*—Hung Xuan Dang
*Attorney, Agent, or Firm*—Fitzpatrick, Cella, Harper & Scinto

[57] ABSTRACT

An eye examining apparatus has a plurality of visual target projecting systems provided for left and right eyes. A visual target for an eye to be examined is adapted to be projected onto the eye to be examined by one of the plurality of visual target projecting systems, the visual target unit for the eye to be examined having a visual target mark for optometry. A visual target for the other eye adapted to be projected onto the other eye by one of the plurality of visual target projecting systems. The visual target for the other eye is provided with the same visual target mark as the visual target for optometry except that the visual target mark is made non-directional.

13 Claims, 18 Drawing Sheets

FIG.35
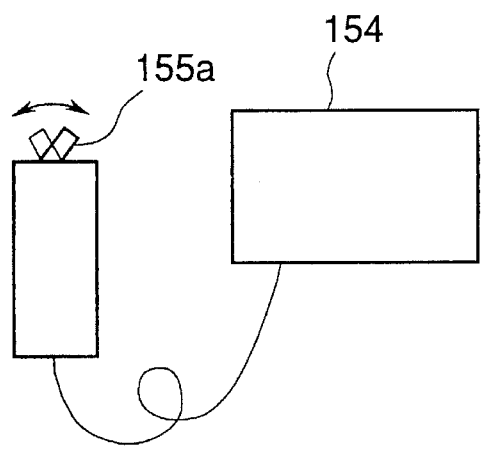
FIG.36A    FIG.36B
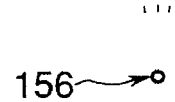    
FIG.37A    FIG.37B
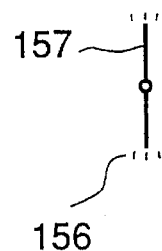    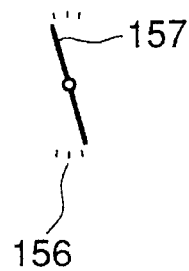

FIG.38A  FIG.38B
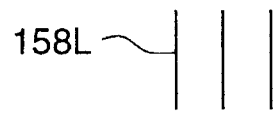
FIG.39
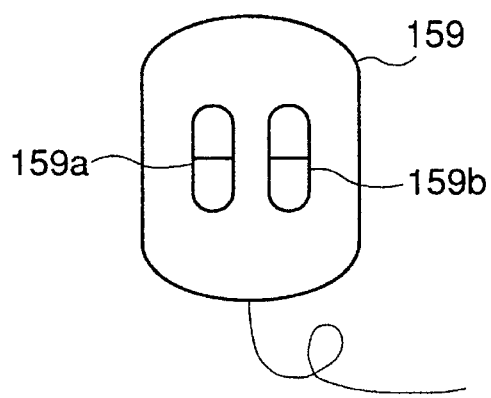
FIG.40
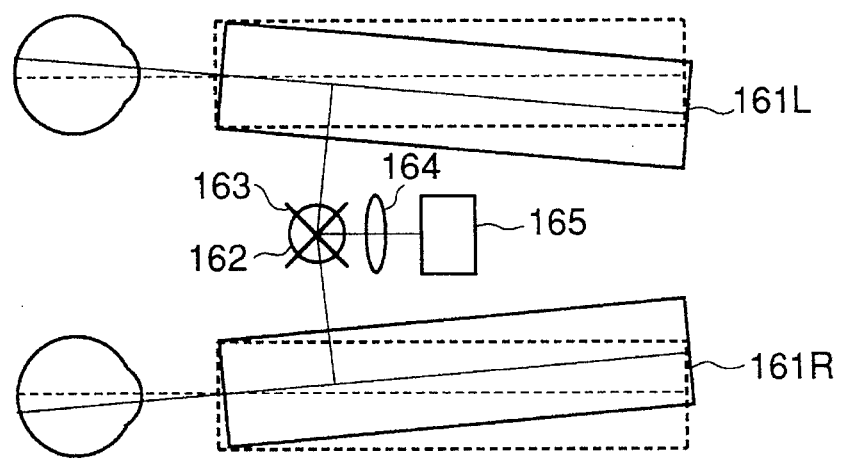

EYE EXAMINING APPARATUS

BACKGROUND OF THE INVENTION

1. Field of the Invention

This invention relates to an eye examining apparatus for measuring eyesight, refractive value, etc., which is used in an ophthalmic clinic or an optician's store.

2. Related Background Art

A conventional objective eye refractometer used with is monocular fixation eye has a drawback in that instrument myopia cannot be completely eliminated.

Japanese Laid-Open Patent Application No. 61-255634 discloses an objective eye refractometer with binocular fixation.

SUMMARY OF THE INVENTION

It is a first object of the present invention to provide an eye examining apparatus which can execute various kinds of eye examinations in a more appropriate form while the eyes to be examined are viewing visual targets binocularly.

It is a second object of the present invention to provide an eye examining apparatus which can measure subjectively eye refractive power or the sight of an eye in a natural state under binocular visual fusion.

It is a third object of the present invention to provide an eye examining apparatus which can effect at one time the enforcement of the same action to the right and left eyes, such as the measurement of binocular visual acuity or induction of accommodation and monocular visual tests in a natural state under binocular visual fusion.

It is a fourth object of the present invention to provide an eye examining apparatus which can effect effective induction of accommodation and eye examination in a natural state under binocular visual fusion.

It is a fifth object of the present invention to provide an eye examining apparatus which can present a visual target of stereoscopic image actually giving a sense of distance to an examinee in a natural state under binocular visual fusion.

BRIEF DESCRIPTION OF THE DRAWINGS

FIG. 35 shows the construction of response input means.

FIGS. 36A and 36B are illustrations of the visual target marks created on the transmission type liquid crystal plate during the examination of cyclophoria.

FIGS. 37A and 37B are illustrations of the central visual target marks viewed binocularly.

FIGS. 38A and 38B are illustrations of the visual target marks created on the transmission type liquid crystal plate.

FIG. 39 is a plan view of measurement input means.

FIG. 40 shows the construction of a fifth embodiment of the present invention.

DESCRIPTION OF THE PREFERRED EMBODIMENTS

Figure 1:
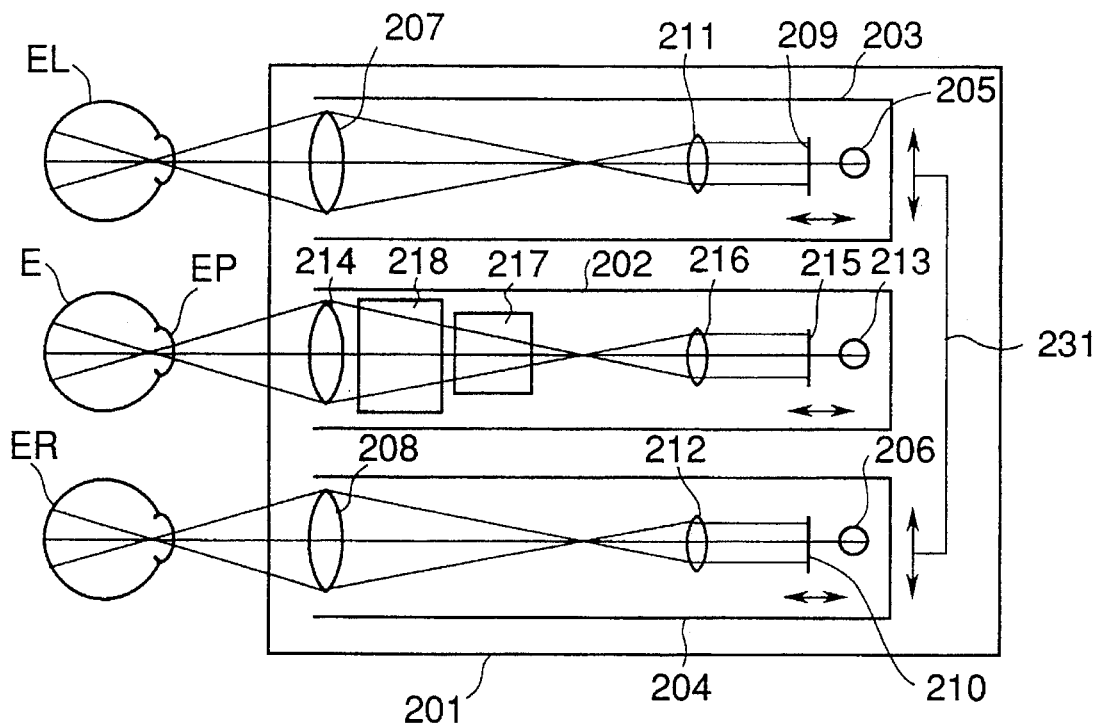
FIG. 1 shows the construction of an optical system as it is seen from above an eye refractometer body according to a first embodiment of the present invention.

The present invention will hereinafter be described in detail with respect to some embodiments thereof shown in the drawings.

Figure 2:
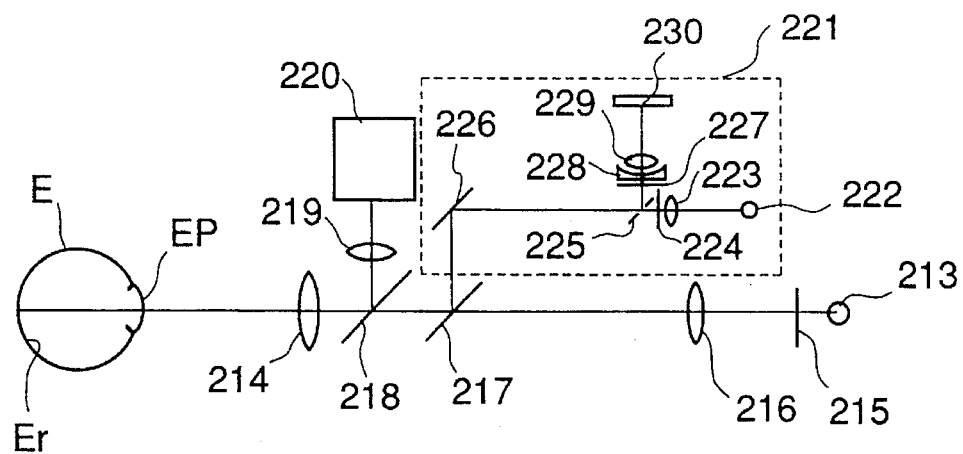
FIG. 2 shows the construction of the optical system as it is seen from a side of the center of the optical system.

Referring to FIG. 1, which shows the construction of the interior of an eye refractometer body 201 according to a first embodiment of the present invention as it is seen from above it, and FIG. 2, which shows the construction of the center of the optical system as it is seen from a side thereof, there are provided a visual target projecting unit 202 for the eye to be examined, and visual target projecting units 203 and 204 for the left eye EL and the right eye ER, respectively. For each eye, on the optical paths leading from the illuminating lamps 205, 206 of the visual target projecting units 203, 204 for the other eye to objective lenses 207, 208, there are provided visual targets 209, 210 to be driven along the optical paths and lenses 211, 212.

As shown in FIG. 2, on the optical path leading from the illuminating lamp 213 of the visual target projecting unit 202 for the eye to be examined to an objective lens 214, there are disposed a visual target 215 to be driven along the optical path, a lens 216 and dichroic mirrors 217, 218, and on the optical path in the direction of reflection of the dichroic mirror 218, there are disposed a lens 219 and a TV camera 220. Also, on the optical path in the direction of reflection of the dichroic mirror 217, there is disposed a measuring unit 221 for objective eye refraction, and on the optical path leading from a light source 222 for measurement within the measuring unit 221 for objective eye refraction to the dichroic mirror 217, there are disposed a lens 223, a stop 224, an apertured mirror 225 and a mirror 226, and on the optical path in the direction of reflection of the apertured mirror 225, there are disposed a multiaperture stop 227, a separating prism 228, a lens 229 and an image pickup element 230.

Figure 3:
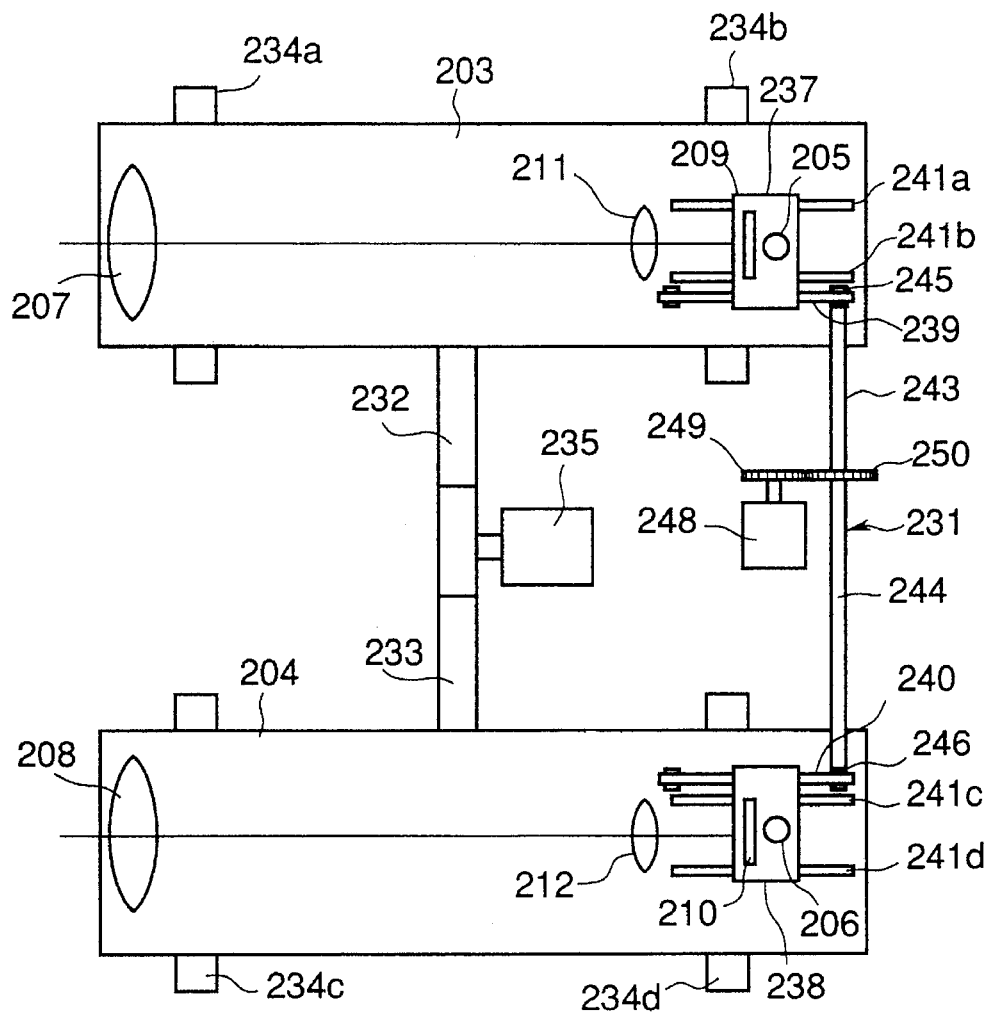
FIG. 3 shows the construction of cooperating means of the plural visual target projecting units.
Figure 4:
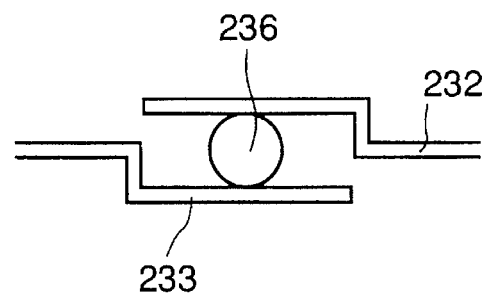
FIG. 4 illustrates the state of engagement between connecting members and a shaft.

Further, the visual target projecting units 203 and 204 for each eye are designed to be moved to left and right by cooperating means 231 of the visual target projecting unit. FIG. 3 shows the construction of this cooperating means 231 of the visual target projecting unit, and as shown, the visual target projecting units 203 and 204 for each eye are connected to connecting members 232 and 233, respectively, and are placed on guide rails 234a–234d. As shown in FIG. 4, the connecting members 232 and 233 are engaged with a shaft 236 to be driven by a drive motor 235. The illuminating lamp 205 and visual target 209 of the visual target projecting unit 203 for one other eye and the illuminating lamp 206 and visual target 210 of the visual target projecting unit 204 for second other eye are provided on members 237 and 238, respectively, which are fixed at one end to belts 239 and 240, respectively, and are movable in the direction of the optical axis along guide rails 241a–241d. The belts 239 and 240 are wound at one end on pulleys 245 and 246, respectively, provided on two shafts 243 and 244, respectively.

Figure 5:
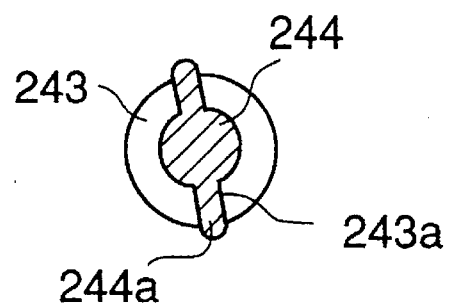
FIG. 5 illustrates the joined state of the shaft.

As shown in FIG. 5, the joined portion of the shafts 243 and 244 are axially expansible and contractible with projections 244a of the shaft 244 engaged with the cut-ins 243a of the shaft 243. Further, a gear 250 meshing with a gear 249 provided on the shaft of a drive motor 248 is fixed on the shafts 243 and 244.

Figure 6:
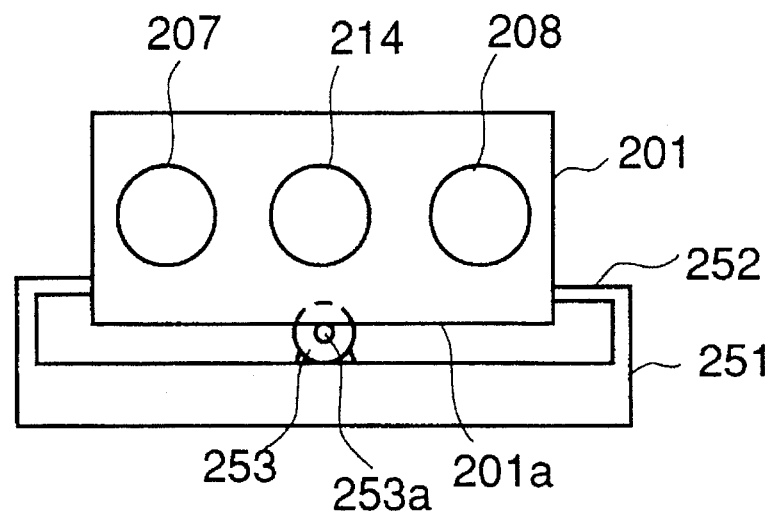
FIG. 6 shows the construction of a mechanism for measuring the pupil distance.

The eye refractometer body 201, as shown in FIG. 6, is provided on a fixed base 251, and is slidable along a guide member 252. A potentiometer 253 is secured to the fixed base 251, and the shaft 253a thereof is rotatable while being in contact with the bottom surface 201a of the eye refractometer body 201.

Figure 7:
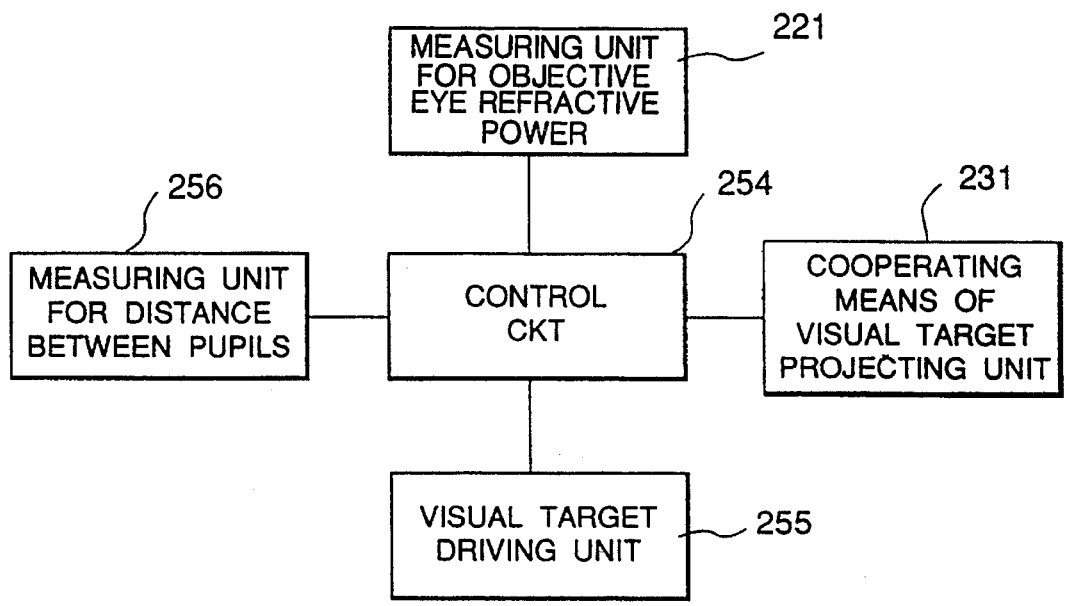
FIG. 7 is a block diagram of a control circuit.

There is also provided a control circuit for controlling the cooperating means 231 of the visual target projecting unit, etc. FIG. 7 is a block diagram of the control circuit, and as shown, the control circuit 254 has connected thereto the measuring unit 221 for objective eye refraction, the cooperating means 231 of the visual target projecting unit to be driven by a drive motor 237 shown in FIG. 3, visual target driving means 255 to be driven by the drive motor 248, and a measuring unit 256 for measuring the distance between pupils comprising the potentiometer 253 shown in FIG. 6, etc.

The distance between pupils is first measured during the measurement of eye refraction. The optical axis of the visual target projecting unit 202 for the eye to be examined is registered with the respective visual axes of the right eye ER and left eye EL while the eye refractometer body 201 is guided by sliding to the left and right along the guide member 252 shown in FIG. 6. At this time, by the eye refractometer body 201 being guided to the to left and right, the shaft 253a of the potentiometer 253 is rotated, and the amount of this rotation is converted into the amount of movement of the eye refractometer body 201 in the measuring unit 256 and the distance between the pupils is found.

The alignment of the visual target projecting unit 202 for the eye to be examined is effected while the anterior eye parts of the right eye ER and left eye EL are observed. The beams of light from the anterior eye parts pass through the lens 214, the dichroic mirror 218 and the lens 219 and are picked up as anterior eye part images by the TV camera 220, and are displayed on a TV monitor, not shown. The examiner can effect the alignment while observing this TV monitor.

The result of the measurement in the measuring unit 256 for distance between pupils by the output of the potentiometer 253 is outputted to the control circuit 254, and on the basis of this result, the cooperating means 231 of the visual target projecting unit is driven and the spacing between the visual target projecting units 203 and 204 for each other eye is adjusted in conformity with the pupil distance. When the drive motor 235 is started, the shaft 236 is rotated to thereby move the connecting members 232 and 233 in opposite directions, whereby the spacing between the visual target projecting units 203 and 204 for each other eye is widened or narrowed. The shafts 243 and 244 are also expanded or contracted with the movement of the visual target projecting units 203 and 204 for each other eye.

The measuring unit 256 detects whether the eye E to be examined is the right eye ER or the left eye EL, and when the eye refractometer body 201 is guided and the left eye EL is aligned with the visual target projecting unit 202 for the eye to be examined, the visual target projecting unit 204 for the other eye moved in advance by the cooperating means 231 of the visual target projecting unit automatically coincides with the right eye ER. Also, where the right eye ER is the object of measurement, when the visual target projecting unit 202 for the eye to be examined is aligned with the right eye ER, the visual target projecting unit 203 for the other eye will automatically coincide with the left eye EL.

When the illuminating lamps 205, 206 and 213 are turned on, the beams of light from the illuminating lamps 205 and 206 illuminate the visual targets 209 and 210, respectively, and pass through the lenses 211 and 212, respectively, and are projected onto the fundus Er of the eye E to be examined. The beam of light from the illuminating lamp 213 passes through the lens 216, the dichroic mirrors 217, 218 and the lens 214 and is projected onto the fundus Er of the eye E to be examined. The visual targets 209, 215 or the visual targets 210, 215 are presented to both eyes, and the fixation of both eyes is done.

Figure 8:
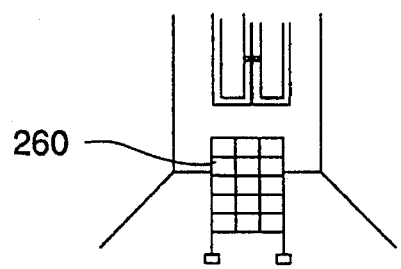
FIG. 8 is an illustration of a background picture of a visual target for optometry.

As regards the visual targets 209, 210 and 215, as shown in FIG. 8, a visual target 260 for optometry is disposed in the room, and subjective eye refraction measurement is effected simultaneously with objective eye refraction measurement.

Figures 9A, 9B, 9C:
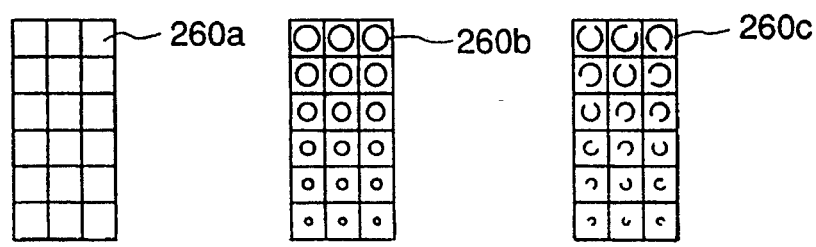
FIGS. 9A, 9B and 9C are front views of visual target marks for optometry.

The visual target 260 for optometry, as shown in FIGS. 9A, 9B and 9C, comprises visual targets 260a for the other eye consisting of frames alone, visual targets 260b for the other eye comprising continuous rings, and visual targets 260c for the eye to be examined comprising Landolt rings. The visual targets 260a and 260b are presented from one of the visual target projecting units 203 and 204 for the other eye and the visual targets 260c are presented from the visual target projecting unit 202 for the eye to be examined, and both eyes view the visual target 260 for optometry. The visual targets 260a and 260b are only for visual fusion and only the eye E to be examined views the visual targets 260c for measurement. The eye reactive value is measured from response to the smallest Landolt rings of the visual targets 260c. Here, a cross cylinder may be inserted into the visual target projecting unit 202 for the eye to be examined to thereby correct astigmatism.

Figure 10:
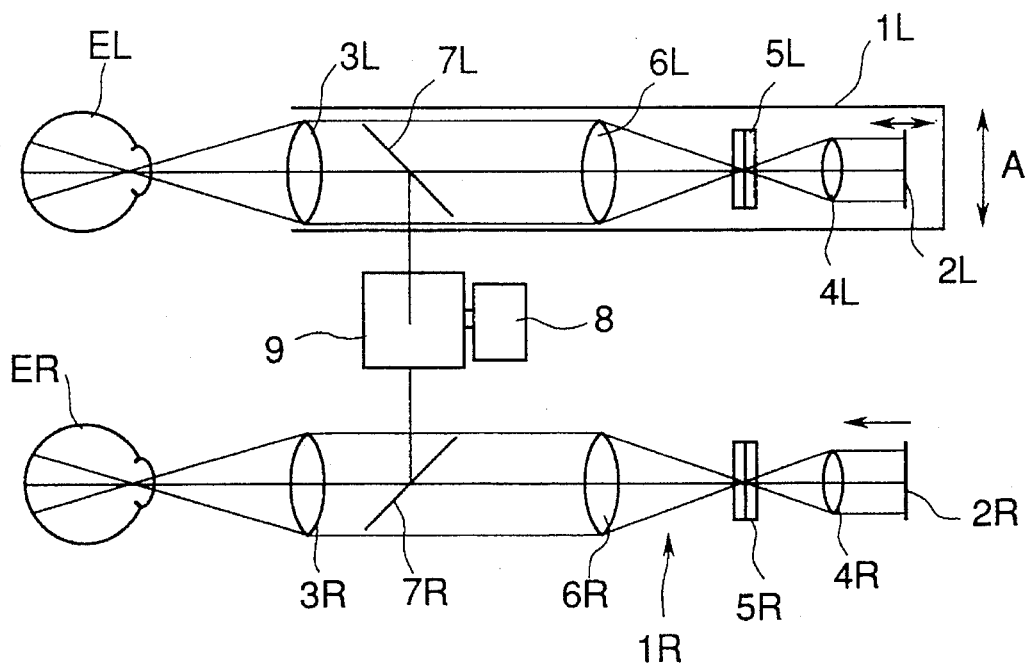
FIG. 10 shows the construction of a visual target optical system in a second embodiment of the present invention.
Figure 11:
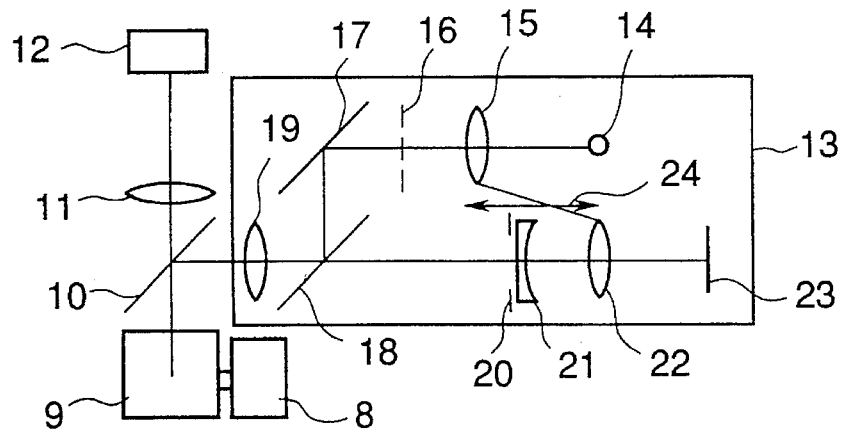
FIG. 11 shows the constructions of an anterior eye part observation system and an objective refractive power measuring system of the second embodiment.

FIGS. 10 and 11 show the construction of a second embodiment of the present invention. As shown in FIG. 10, visual target optical systems 1L and 1R for the left eye EL and right eye ER are provided parallel to each other in a measuring head, not shown, and the visual target optical system 1L for the left eye EL is movable in the directions of arrow A so as to adjust the spacing between the visual target optical systems 1L and 1R for the left eye EL and right eye ER respectively. The optical members of the visual target optical systems 1L and 1R are disposed symmetrically, and on the optical paths leading from visual targets 2L, 2R movable along the optical axes to lenses 3L, 3R, there are disposed lenses 4L, 4R, cross cylinders 5L, 5R comprising cylindrical lenses having the same refractive power, lenses 6L, 6R and dichroic mirrors 7L, 7R, and on the optical path linking the dichroic mirrors 7L and 7R together, there is disposed a mirror 9 to be driven by a solenoid 8.

Figure 12:
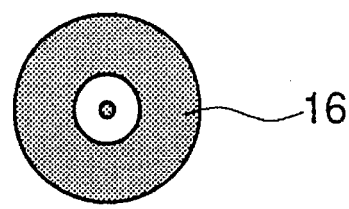
FIG. 12 is a front view of a ring stop.
Figure 13:
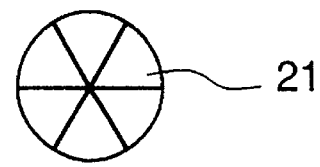
FIG. 13 is a front view of a separating prism.

FIG. 11 shows a side section of the above system. As shown in FIG. 11, on the optical path in the direction of reflection of the mirror 9, i.e., the upward direction, there are disposed a dichroic mirror 10, a lens 11 and a near infrared TV camera 12. Also, on the optical path in the direction of reflection of the dichroic mirror 10, there is disposed an objective refractive power measuring system 13, and on the optical path leading from a refractive power measuring light source 14 such as an LED to the dichroic mirror 10, there are disposed a lens 15, a ring stop 16 having a ring-shaped opening as shown in FIG. 12, a mirror 17, a half mirror 18 and a lens 19, and further on the optical path behind the half mirror 18, there are disposed a six-aperture stop 20, a separating prism 21 as shown in FIG. 13, a lens 22 and a photoelectric sensor 23, and driving means 24 for driving the lenses 15 and 12 as a unit along the optical axis is provided.

The ring stop 16, the six-aperture stop 20 and the cross cylinder lenses 5L, 5R are disposed at locations conjugate with the pupil of the eye to be examined, and the dichroic mirrors 7L and 7R each have a wavelength dividing characteristic of transmitting visible light therethrough and reflecting infrared light. Also, the measuring head containing therein the optical system shown in FIG. 11 is provided on a slidable stand, not shown, and is movable in vertical and horizontal directions.

When the anterior eye part is to be observed, the beams of light from the anterior eye parts of the left eye EL and right eye ER pass through the lenses 3L and 3R, respectively, and are collimated thereby and are reflected by the dichroic mirrors 7L and 7R, respectively. The selection of the eye to be observed is effected by the mirror 9 being rotated by the solenoid 8, and where the left eye EL is to be observed, the mirror surface of the mirror 9 may be opposed to the dichroic mirror 7L, and where the right eye ER is to be observed, the mirror surface of the mirror 9 may be turned to the dichroic mirror 7R. The beam of light reflected from the dichroic mirror 7L or the dichroic mirror 7R is reflected by the mirror 9, passes through the dichroic mirror 10 and the lens 11, is imaged as an anterior eye part image on the image pickup surface of the near infrared TV camera 12, and is displayed on a TV monitor, not shown. The examiner moves the measuring head, not shown, and the visual target optical system 1L for the left eye EL to thereby align the visual target optical systems 1L and 1R for the left eye EL and right eye ER with the left eye EL and right eye ER while observing the TV monitor. The image pickup surface of the near infrared TV camera 12 is on the focal plane of the lens 11 and the beams of light from the anterior eye parts are collimated by the lenses 3L and 3R and arrive at the lens 11 and therefore, even if the spacing between the visual target optical systems 1L and 1R for the left eye EL and right eye ER is varied, the focuses of the anterior eye part images will be kept.

When objective refractive power measurement is to be effected, the mirror 9 is rotated by the solenoid 8 to thereby effect the selection of the eye to be examined as during the observation of the anterior eye parts. When the refractive power measuring light source 14 shown in FIG. 11 is turned on after the termination of alignment, the beam of light from the refractive power measuring light source 14 passes through the lens 15 and the ring stop 16, is reflected by the mirror 17 and the half mirror 18, passes through the lens 19 and is reflected by the dichroic mirror 10 and the mirror 9. The beam of light from the mirror 9 is reflected by one of the dichroic mirrors 7L and 7R to which the mirror surface of the mirror 9 is opposed, and passes through the lens 3L or the lens 3R and is projected in the form of a point onto the fundus of the left eye EL or right eye ER.

Figure 14:
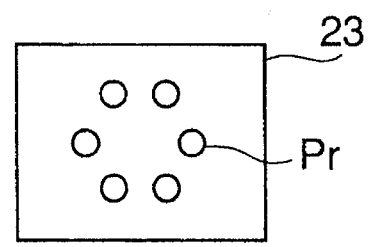
FIG. 14 is an illustration of an eye fundus reflected light beam image received by a photoelectric sensor.

The reflected beam of light from the fundus of the left eye EL or right eye ER returns along the same optical path, is reflected by the mirror 9 and the dichroic mirror 10, passes through the lens 19, the half mirror 18, the six-aperture stop 20, the separating prism 21 and the lens 22, and is formed as an eye fundus reflected light beam image Pr comprising six small circles as shown in FIG. 14, on the photoelectric sensor 23. The refractive power of the eye E to be examined is calculated from the received position of the eye fundus reflected light beam image Pr and the positions of the lenses 15 and 22. The focusing of the eye fundus reflected light beam image Pr is effected by the lenses 15 and 22 being moved along the optical axis by the driving means 24.

The ring stop 16 conjugate with the pupil and the separating prism 21 are disposed on the focal plane of the lens 19 and therefore, even if the visual target optical system 1L for the left eye EL is moved to adjust the eye width, the focal plane of the lens 19 will not deviate from the ring stop 16 and the separating prism 21, while the focal plane relative to the fundus of the eye will deviate from the ring stop 16 and the separating prism 21 and therefore, when the eye to be examined is the left eye EL, it is necessary to calculate the refractive power with the position of the visual target optical system 1L for the left eye EL taken into account.

Heretofore, in objective refractive power measurement, only a part of the pupil has been used to project a beam of light onto the fundus of the eye and therefore, when there is an aberration in the pupil of the eye to be examined, the result of the measurement may differ from the result of the measurement of subjective refractive power effected by the use of the whole area of the pupil, but the objective refractive power measuring system 13 shown in FIG. 11 uses the whole area of the pupil, and this leads to the merit that accurate measurement can be accomplished.

When subjective refractive power measurement is to be effected, both eyes are made to look into the visual target optical systems 1L and 1R for the left eye EL and right eye ER. The beams of light from the visual targets 2L, 2R pass through the lenses 4L, 4R, the cross cylinder lenses 5L, 5R, the lenses 6L, 6R, the dichroic mirrors 7L, 7R and the lenses 3L, 3R to the funduses of the left eye EL and right eye ER. The visual targets 2L and 2R are moved along the optical axes to thereby vary the apparent diopter of the visual targets 2L and 2R, and the examinee's diopter is guided. At this time, the two cylindrical lenses of the cross cylinders 5L and 5R can be rotated independently of each other to thereby insert the degree of astigmatism and the astigmatic angle.

Figure 15:
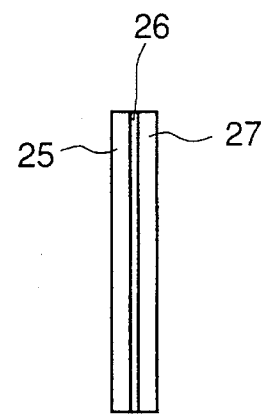
FIG. 15 is a side view of a visual target for right and left eyes.
Figure 16:
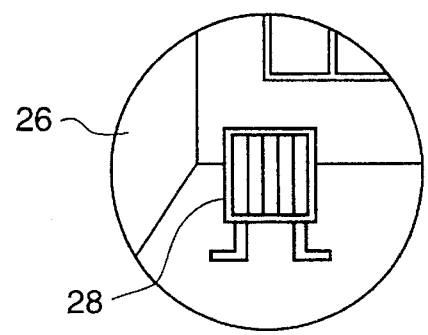
FIG. 16 is a front view of a color slide.

The visual targets 2L and 2R, as shown in FIG. 15, are comprised of three members, i.e., cover glass 25, a color slide 26 shown in FIG. 16, and a glass plate 27 printed with a visual target by a method such as etching. The cover glass 25 and the color slide 26 are members common to the visual targets 2L and 2R for the left eye EL and right eye ER, and the color slide 26 is a slide photograph which has taken the manner in which a visual target plate 28 for optometry is placed at a far distance, but the visual target mark is not imaged on this visual target plate 28, but only a frame is imaged thereon.

Figure 17:
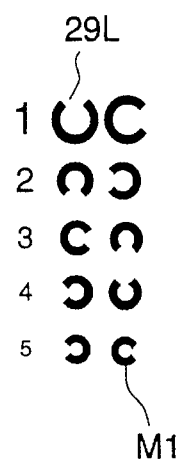
FIG. 17 illustrates visual target marks for the left eye.
Figure 18:
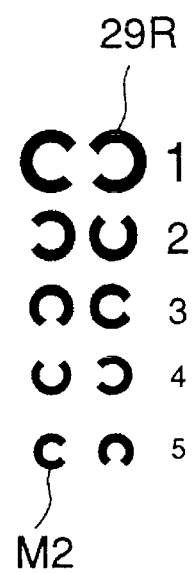
FIG. 18 illustrates visual targets for the right eye.

Since it is difficult to make a visual target plate including visual target marks by photography, the visual target marks may be prepared separately and combined with a background picture. On the other hand, visual target marks 29L and 29R comprising Landolt rings and numerals are provided on the glass plate 27 as shown in FIGS. 17 and 18. The marks of 29L, 29R are different from each other, and only visual target marks M1 in the rightmost column of the visual target marks 29L for the left eye EL shown in FIG. 17 and visual target marks M2 in the leftmost column of the visual target marks 29R for the right eye ER shown in FIG. 18 are common to each other.

Figure 19:
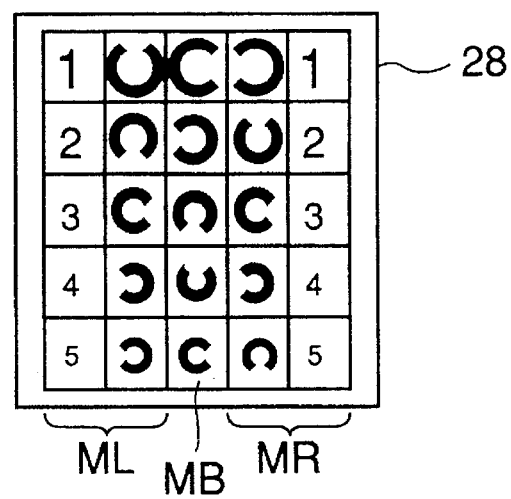
FIG. 19 is an illustration of a visual target viewed at by an examinee.

When the examinee is made to fixate on the visual targets 2L and 2R shown in FIGS. 16 to 18 with both eyes, the examinee feels as if the visual target plate 28 shown in FIG. 19 was placed at a far distance in the room shown in FIG. 16 and therefore, the examinee is made to fixate at the visual targets 28 on the visual target plate and the refractive power is obtained from the response of the smallest visually confirmed visual target. At this time, the central visual targets MB are viewed by both eyes, the visual targets ML in the left two columns are viewed by the left eye EL, and the visual targets MR in the right two columns are viewed by the right eye ER. Therefore, for a binocular test, visual target marks MB are used, and for a monocular test, the visual target marks ML in the left two columns and the visual target marks MR in the right two columns are used. This monocular test is done with binocularly fused vision.

Also, when objective refractive power measurement is to be effected, the angles of rotation of the cross cylinder lenses 5L and 5R and the positions of the visual targets 2L and 2R are determined from the value of objective refractive power, and the guide of diopters is effected by the use of the visual targets 2L and 2R. Objective refractive power measurement is effected with the positions of the visual targets 2L and 2R somewhat deviated toward the long-distance viewing side while the examinee is made to visually confirm the smallest visual targets of the visual targets 2L and 2R. If at this time, the examinee's diopters follow the diopters of the visual targets 2L and 2R, then the cross cylinder lenses 5L, 5R and the visual targets 2L, 2R are again adjusted and objective refractive power measurement is again effected. By repeating this step, objective refractive power from which the adjustment of the eyes has been eliminated can be measured.

In the prescription of spectacles, it is necessary to determine the degree of spherical refractive power to be inserted for a correction lens for providing necessary corrected eyesight or to determine how to correct astigmatism, and judgment can be done from the result of optometry, and in subjective refractive power measurement, the angles of rotation of the cylindrical lenses of the cross cylinder lenses 5L and 5R are varied to thereby adjust the degree of cylindrical power and the positions of the visual targets 2L and 2R are varied to thereby adjust the degree of spherical power, whereby the degree of power and the degree of spherical power to be corrected can be determined. If for example, the examinee's degree of astigmatism is weak and the examinee's eyesight is Good, only the correction of spherical power will be effected.

Figure 20:
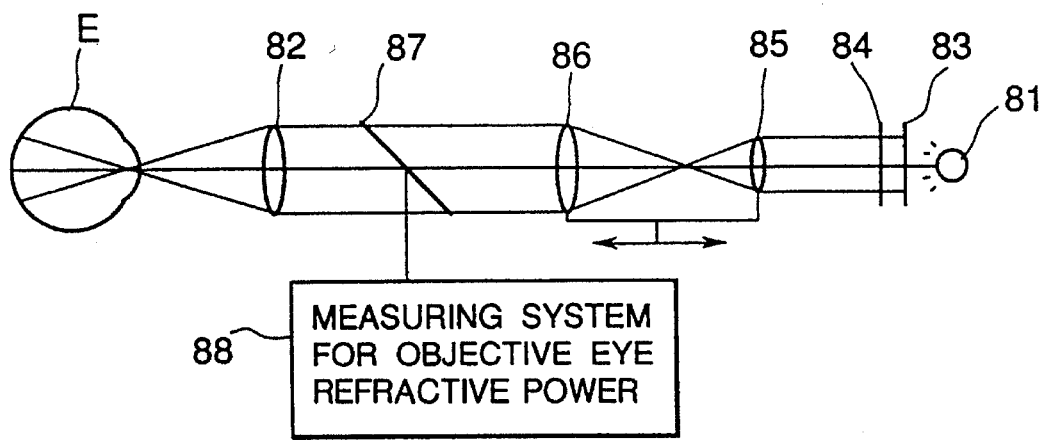
FIG. 20 illustrates the principle of a third embodiment of the present invention.

FIG. 20 shows the principle of a third embodiment of the present invention. As shown, on the optical path leading from a light source 81 to an objective lens 82, there are disposed a distant visual target 83 comprising a slide photograph, a near visual target 84, diopter guiding lenses 85, 86 movable as a unit along the optical axis, and a dichroic mirror 87, and on the optical path in the direction of reflection of the dichroic mirror 87, there is disposed an objective refractive power measuring system 88.

A parallel beam of light from the light source 81 passes through the distant visual target 83 and near visual target 84, passes through the diopter guiding lens 85 and is once imaged, and passes through the diopter guiding lens 86 and is again made into a parallel beam of light, which passes through the dichroic mirror 87 and the objective lens 82 and is projected onto an eye E to be examined, and the visual targets are presented to the eye E to be examined.

Figures 21A, 21B, 21C:
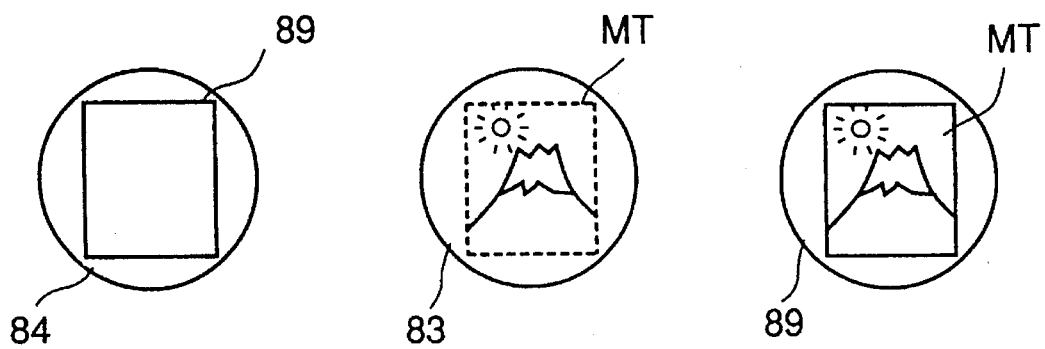
FIGS. 21A, 21B, and 21C are illustrations of a near visual target and a far visual target.

The near visual target 84, as shown in FIG. 21A, comprises a window frame 89 surrounding a rectangular transparent portion, and in the distant visual target 83, as shown in FIG. 21B, the portion thereof corresponding to the rectangular transparent portion of the near visual target 84 is a mountain-scape MT. Accordingly, the eye E to be examined as if it was fixating at the mountain-scape MT surrounded by the window frame 89 as shown in FIG. 21C, feels the window frame 89 as a near view and the mountain-scape MT as a distant view and thus, and it is easy to obtain the sense of distance. The apparent diopters of the distant visual target 83 and near visual target 84 are adjusted by the diopter guiding lenses 85 and 86 being moved along the optical axis, but even if the positions of the diopter guiding lenses 85 and 86 are changed, the relation between the window frame 89 of the near visual target 84 and the mountain-scape MT of the distant visual target 83 will be kept at a constant diopter.

After the diopter guide is terminated, a refractive power measuring light source provided in the objective refractive power measuring system 88 is turned on. The beam of light from the refractive power measuring light source is reflected by the dichroic mirror 87, passes through the objective lens 82 and is projected onto the fundus of the eye E to be examined. The reflected beam of light from the fundus of the eye returns along the same optical path and is received by the objective refractive power measuring system 88, whereby the refractive power is calculated.

Figure 22:
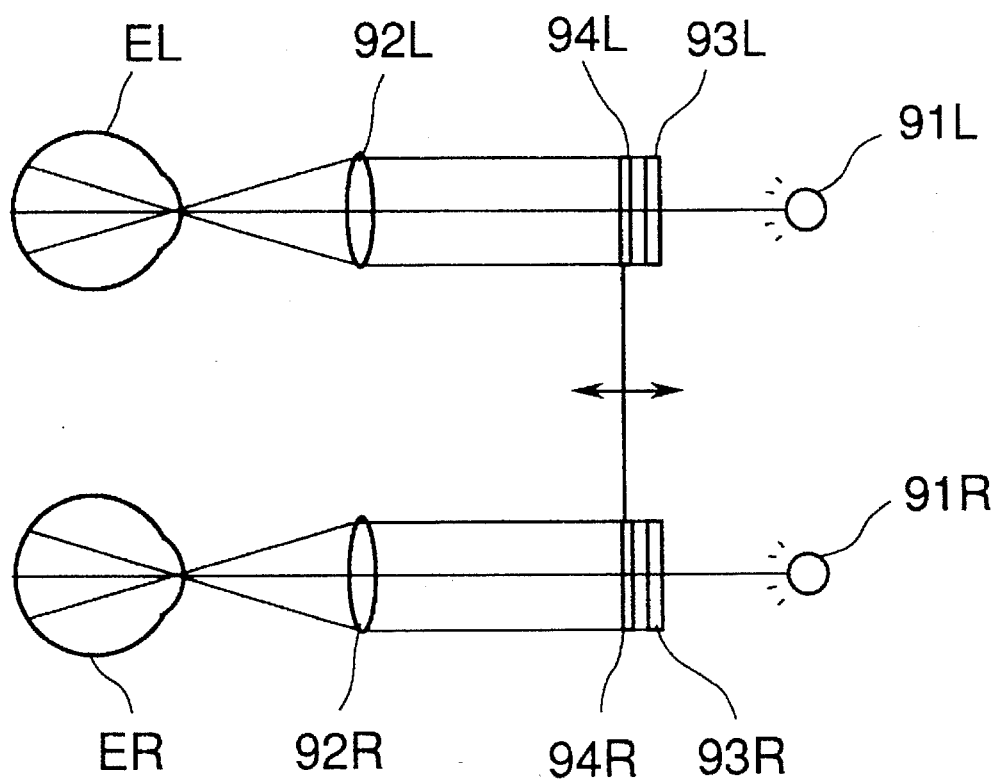
FIG. 22 shows the a construction of the third embodiment.

FIG. 22 shows the construction of the third embodiment, which is provided with discrete visual target optical systems for the left eye EL and right eye ER. On the optical paths leading from light sources 91L, 91R to objective lenses 92L, 92R, there are disposed distant visual targets 93L, 93R each comprising liquid crystal display means for a displaying computer graphic, and near visual targets 94L, 94R. The near visual targets 94L, 94R are movable as a unit along the optical axes.

When the light sources 91L and 91R are turned on, the distant visual targets 93L, 93R and near visual targets 94L, 94R illuminated from behind them are presented to the examinee's left eye EL and right eye ER through the objective lenses 92L and 92R, respectively, and the accommodation both eyes of the examinee are induced. Those portions of the near visual targets 94L, 94R which overlap the distant visual targets 93L, 93R are transparent portions, and no image is displayed thereon. Also, computer graphics displayed on the distant visual targets 93L, 93R and near visual targets 94L, 94R are images (stereoscopic images) accompanied by the parallaxes of the left eye EL and right eye ER. That is, the distance between the visual targets 94L and 94R are closer than that between the visual target 93L and 93R. Accordingly, by the near visual targets 94L, 94R being moved back and forth along the optical axes, the parallaxes of the left eye EL and right eye ER are varied and at the same time, the apparent diopters of the distant visual targets 93L, 93R and near view visual targets 94L, 94R are varied and therefore, a more natural sense of distance can be given to the examinee.

While in this embodiment, two visual targets are provided in respective ones of the discrete visual target optical systems for the left eye EL and right eye ER, a greater number of visual targets may be provided, and the visual targets may be fixed visual targets. Also, the distant view visual targets 93L, 93R may be comprised of CRT instead of a liquid crystal display means.

Figure 23:
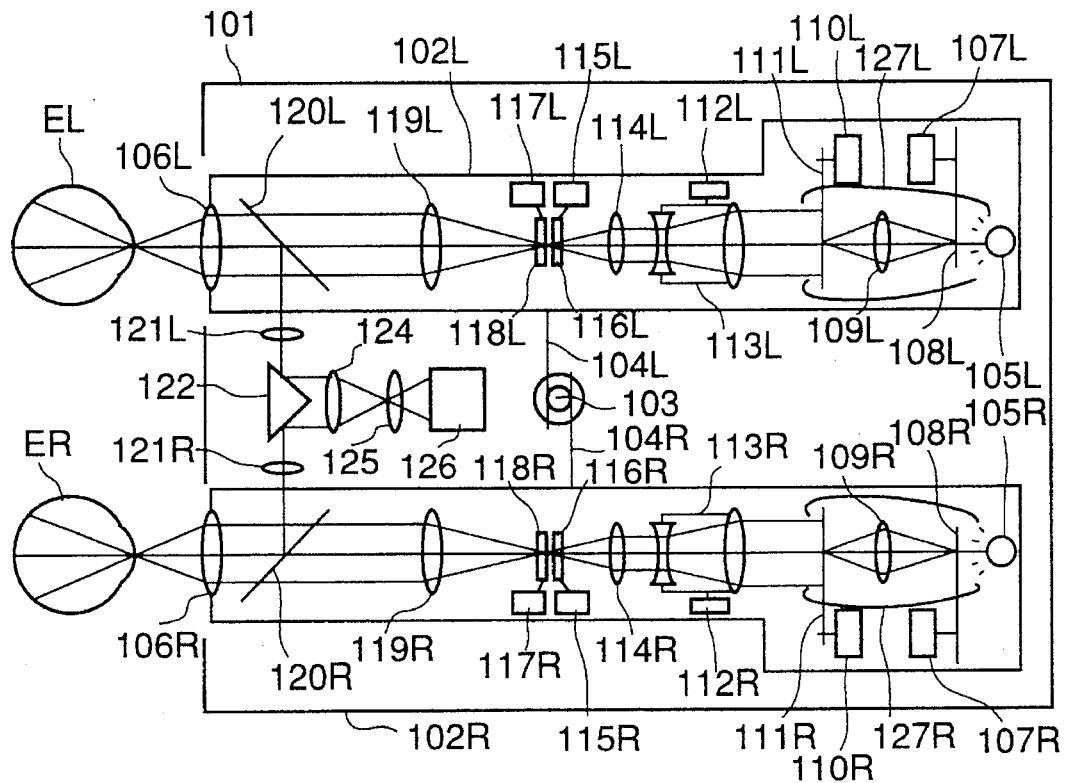
FIG. 23 shows the construction of a fourth embodiment of the present invention.

FIG. 23 shows the construction of a fourth embodiment of the present invention. As shown, visual target optical systems 102L and 102R for the left eye EL and right eye ER are provided parallel to each other in a measuring head 101, and are connected together for movement to the left and right by joint members 104L and 104R connected to a step motor 103. On the optical path leading from a light source 105L disposed in the visual target optical system 102L for the left eye EL to an objective lens 106L, there are disposed a central visual target plate 108L shown in FIG. 24 which is rotated by driving means 107L, a relay lens 109L, a marginal visual target plate 111L rotated by driving means 110L, a diopter varying lens system 113L comprising two lenses driven along the optical axis by driving means 112L, a lens 114L, a cross cylinder 116L comprising two cylindrical lenses of the same refractive power rotated by driving means 115L, a rotatable prism 118L comprising two prisms of the same refractive power rotated by driving means 117L, a lens 119L and a dichroic mirror 120L having a characteristic of reflecting near infrared light, and corresponding optical members are disposed in the visual target optical system 102R for the right eye ER.

Also, on the optical path linking the dichroic mirrors 120L and 120R together, there are disposed a lens 121L, a prism 122 and a lens 121R, and on the optical path behind the prism 122, there are provided a field lens 124, a relay lens 125 and a TV camera 126 for observation secured to the head 101. There are also provided a pair of optical fibers 127L and a pair of optical fibers 127R for illuminating the marginal visual target plates 111L and 111R by the light sources 105L and 105R, respectively. The two lenses of the diopter varying lens systems 113L and 113R are spaced apart by the sum of their focal lengths. The lenses 114L and 114R are located so that their anterior focal points are conjugate to the rotatable prism as well as the pupils of the eyes. The rotatable prisms and the objective lenses 106L and 106R are located so that their anterior focal points coincide with the pupils.

Figure 24:
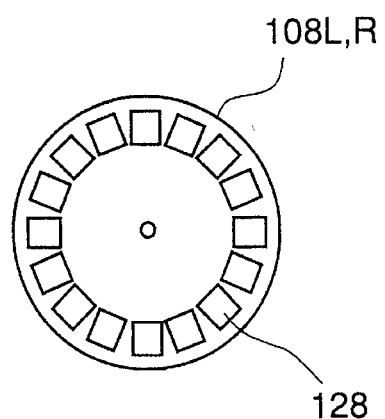
FIG. 24 is a front view of a central visual target plate.
Figure 25:
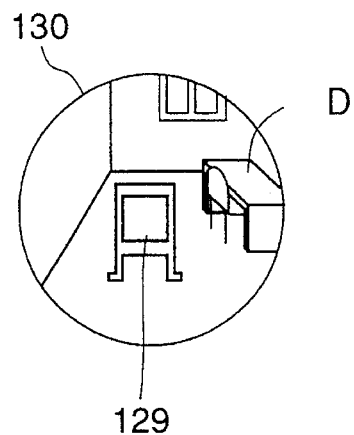
FIG. 25 is a front view of a far vision target.
Figure 26:
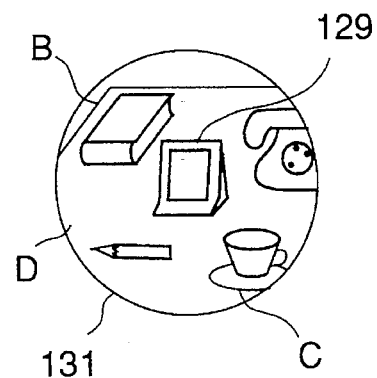
FIG. 26 is a front view of a near vision target.

Also, a plurality of central visual targets 128 are provided on the marginal edge portion of each of the disc-like central visual target plates 108L, 108R as shown in FIG. 24, and these central visual targets 128 comprise visual targets common to the left eye EL and right eye ER, partially common visual targets, and visual targets different for the left eye EL and right eye ER, and by the central visual target plates 108L and 108R being rotated by the driving means 107L and 107R, respectively, those of the central visual targets 128 which conform to purposes such as optometry, refractive power measurement and both-eye examination are inserted into the optical path. On the other hand, on the marginal visual target plates 111L and 111R, there are provided a distant visual target 130 which is the photograph of a visual target plate 129 installed in the room as shown in FIG. 25, and a near visual target 131 which is the photograph of a visual target plate 129 placed on a desk D as shown in FIG. 26, and the marginal visual target plates 111L and 111R are rotated by the driving means 110L and 110R, respectively, whereby the distant visual target 130 and the near visual target 131 to be inserted into the optical path can be changed over.

The distant visual target 130 and near visual target 131 are a set of stereoscopic photographs for the left eye EL and right eye ER, and when the examinee is made to fixate at the distant visual target 130, there occurs the parallax of the left eye EL and right eye ER due to the desk D farther that the visual target plate SB, and when the examinee is made to fixate at the near visual target 131, there occurs the parallax of the left eye EL and right eye ER due to the coffee cup C ahead of the visual target plate 129 and the book B behind the visual target plate 129 and therefore, the examiner can obtain a natural stereoscopic sense and the sense of distance can be readily created.

Figure 27:
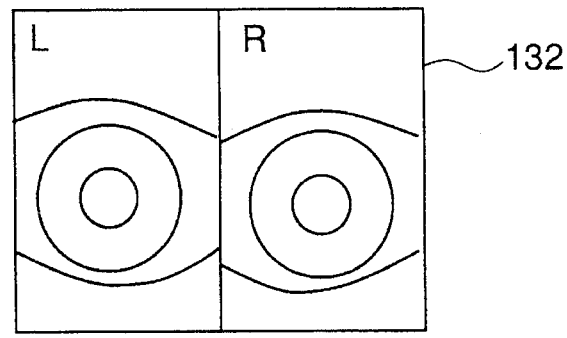
FIG. 27 illustrates an anterior eye part images displayed on a TV monitor.

When the observation of the anterior eye parts is to be done, the beam of light from the anterior eye parts of the left eye EL and right eye ER pass through the objective lenses 106L and 106R, respectively, and are collimated thereby, and are reflected by the dichroic mirrors 120L and 120R, respectively, and then pass through the lenses 121L and 121R, respectively, and are once imaged on the prism 122, and pass through the field lens 124 and the relay lens 125, and are imaged as the anterior eye parts of the left eye EL and right eye ER on the image pickup element of the TV camera 126 for observation, and the images of the anterior eye parts of the both eyes are displayed at one time on a TV monitor 132, as shown in FIG. 27.

The examiner effects the alignment of the head 101 and the visual target optical systems 102L, 102R for the left eye EL and right eye ER with the left eye EL and right eye ER while observing the TV monitor 132. The examiner first moves the entire head 101 to thereby effect rough alignment, whereafter when the step motor 103 is driven, the joint members 104L and 104R are moved in opposite directions, whereby the spacing between the visual target optical systems 102L and 102R is widened or narrowed and thus, eye width adjustment is done. As the light beams between the lens 106L, 106R and 121L, 121R, respectively, are collimated beams, the width adjustment of the optical systems 102L, 102R does not affect the focus of the anterior eye part images by the TV camera 126.

After termination of the alignment, the driving means 107L, 107R, 110L and 110R are driven to thereby rotate the central visual target plates 108L, 108R and the marginal visual target plates 111L, 111R, and those of the visual targets which conform to the examination purpose are inserted into the optical path. When the light sources 105L and 105R are turned on, the beams of light from the light sources 105 illuminate the central visual target plates 108L, 108R from behind them and at the same time, illuminate the marginal visual target plates 111L, 111R through the optical fibers 127. The beams of light from the central visual target plates 108L, 108R pass through the relay lenses 109L, 109R, the marginal visual target plates 111L, 111R, the diopter varying lens systems 113L, 113R, the lenses 114L, 114R, the cross cylinder lenses 116L, 116R, the variable prisms 118L, 118R, the lenses 119L, 119R, the dichroic mirrors 120L, 120R and the objective lenses 106L, 106R, and are projected onto the funduses of the left eye EL and right eye ER, whereby the visual targets are presented to the left eye EL and right eye ER.

The distant visual target 130 of FIG. 25 and the visual target plate 129 in the central portion of the near visual target 131 of FIG. 26 on the marginal visual target plates 111L and 111R comprise frames alone and the inside thereof is transparent and therefore, the central visual target 128 is projected onto the transparent portion of the visual target plate 129 by the relay lenses 109L, 109R. Accordingly, the examinee feels as if he or she was fixating at the central visual target 128 surrounded by the visual target plate 129.

When the examinee's diopter is to be guided, the diopter varying lens systems 113L and 113R are moved along the optical axes by the driving means 112L and 112R, respectively, to thereby adjust the apparent diopters of the central visual target plates 108L and 108R. The beams of light are made into parallel beams of light before and behind the diopter varying lens systems 113L and 113R and therefore, even if the diopter varying lens systems 113L and 113R are moved along the optical axes, the apparent sizes of the visual targets will not vary. Also, the two cylindrical lenses of the cross cylinder lenses 116L and 116R can be rotated by the driving means 115L and 115R, respectively, to thereby create a degree of astigmatism and an astigmatic angle. Further, the two prisms of the variable prisms 118L and 118R can be rotated by the driving means 117L and 117R, respectively, to thereby deflect the optical axes.

Figure 28:
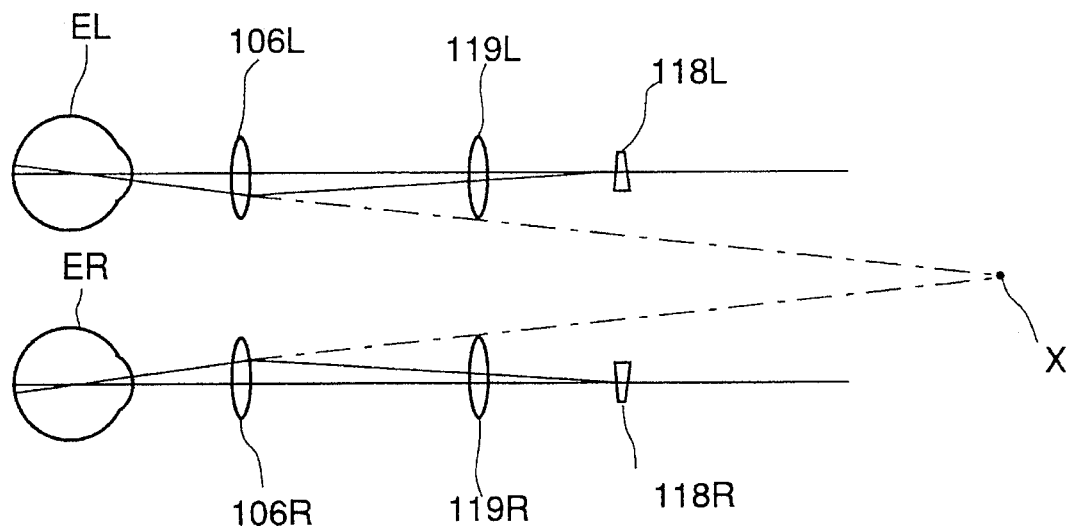
FIG. 28 illustrates the optical axes of near vision examination and the apparent position of a visual target.

For example, when a short-distance viewing examination is to be effected by the use of the near viewing visual targets 131 of the marginal visual target plates 111L and 111R, if the variable prisms 118L and 118R are rotated to incline the optical axes as shown in FIG. 28 so that the visual axes can be converged at a position X, the examinee will feel as if he or she was looking at the visual targets nearby. The variable prisms 118L and 118R can also be used for heterophoria examination or the like as in the prior-art apparatus.

Figure 29:
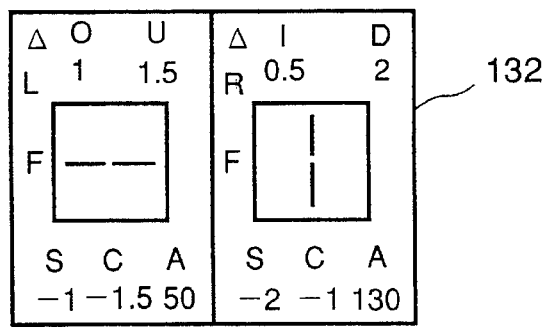
FIG. 29 illustrates the screen of a TV monitor during examination.

In this embodiment, as shown in FIG. 29, the information of the right eye ER is displayed on the right-hand side of the screen of the TV monitor 132 and the information of the left eye EL is displayed on the left-hand side of the screen. The central visual targets 128 of the central visual target plates 108L and 108R being presented to the left eye EL and right eye ER are displayed at the centers of the respective screens, the alphabet characters sideways thereof represent the kind of the visual targets of the marginal visual target plates 111L and 111R being presented to the left eye EL and right eye ER, and the letter F represents that the distant visual target 130 is being presented. Also, in the lower portion of the screen, there are displayed the spherical power S, astigmatic power C and angle A determined by the cross cylinder lenses 116L, 116R and the diopter varying lens systems 113L and 113R, and in the upper portion of the screen, there are displayed the prismatic power determined by the variable prisms 118L and 118R. The examiner effects the selection of the visual targets, the adjustment of the diopters of the visual targets, the insertion of astigmatism, etc. to thereby accomplish a desired examination while observing the TV monitor 132.

Figure 30:
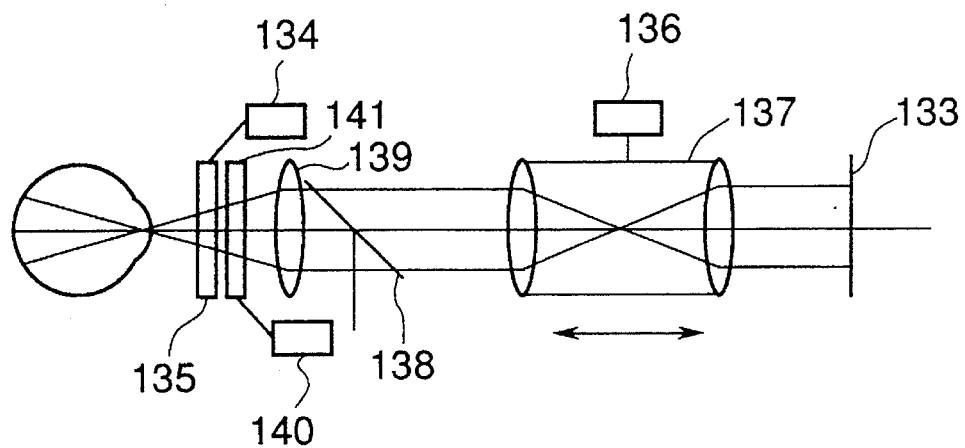
FIG. 30 shows the construction of a first modification of the visual target optical system.

FIG. 30 shows a first modification of the visual target optical systems 102L and 102R for the left eye EL and right eye ER of the apparatus shown in FIG. 23. This modification is constructed so that diopter varying lens systems 113L, 113R and rotatable prisms 118L, 118R are disposed forwardly of objective lenses 106L, 106R, and on the optical path leading from a marginal visual target plate 133 to a rotatable prism 135 comprising two identical prisms driven by driving means 134, there are disposed a diopter varying lens system 137 comprising two convex lenses moved alone the optical axis by driving means 136, a dichroic mirror 138, an objective lens 139 and a cross cylinder lens 141 comprising two cylindrical lenses of the same refractive power driven by driving means 140.

A beam of light from a central visual target plate, not shown, passes through the marginal visual target plate 133, the diopter varying lens system 137, the dichroic mirror 138, the objective lens 141, the cross cylinder lens 141 and the rotatable prism 135 and is projected to the fundus of the eye, and the visual targets are presented to both eyes, whereby a desired examination is effected. The beam of light is made into a parallel beam of light forwardly and rearwardly of the diopter varying lens system 137 and therefore, even if the diopter varying lens system 137 is driven along the optical axis, the apparent size of the visual targets will not vary.

Figure 31:
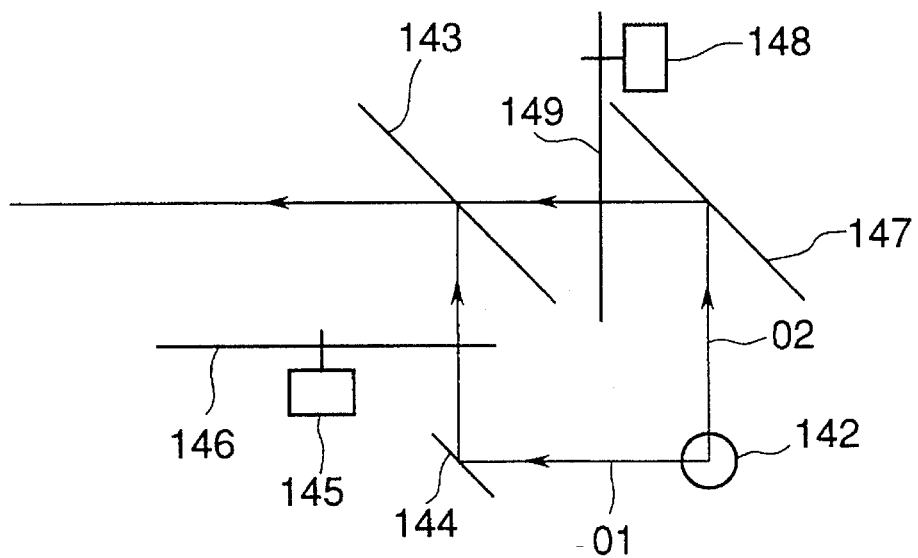
FIG. 31 shows the construction of a second modification of the visual target optical system.

FIG. 31 shows a second modification of the visual target optical systems 102L and 102R for the left eye EL and right eye ER. This modification is constructed so that the optics from the light sources 105L, 105R shown in FIG. 23 to the marginal visual target plates 111L, 111R. On the leftwardly extending optical path 01 leading from a light source 142 to a half mirror 143, there are disposed a mirror 144 and a central visual target plate 146 driven by driving means 145, and on the upwardly extending optical path 02 leading from the light source 142 to the half mirror 143, there are disposed a mirror 147 and a marginal visual target plate 149 driven by driving means 148.

Beams of light from the light source travel in two directions, and one of the two beams of light is reflected by the mirror 144 and illuminates the central visual target plate 145, and the other beam of light is reflected by the mirror 147 and illuminates the marginal visual target plate 149, and the two beams of light are again combined together by the half mirror 143 and projected onto the left eye EL and right eye ER. The visual targets of the central visual target plate 145 and marginal visual target plate 149 are presented as an overlapping image to the left eye EL and right eye ER and therefore, the diopters of the left eye EL and right eye ER can be guided to thereby effect a desired examination.

Figure 32:
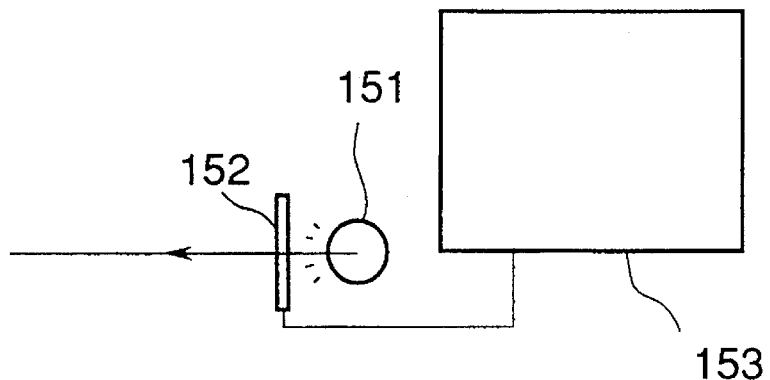
FIG. 32 shows the construction of a modification of the central visual target of a liquid crystal plate.
Figure 33A:
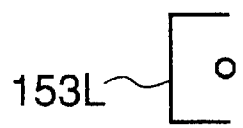
FIGS. 33A and 33B are illustrations of the visual target marks viewed monocularly created on a transmission type liquid crystal plate.
Figure 33B:
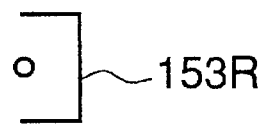
Figure 34A:
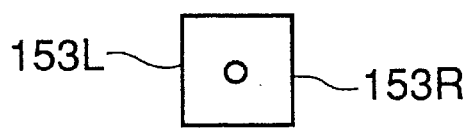
FIGS. 34A and 34B are illustrations of the visual target marks viewed binocularly.
Figure 34B:
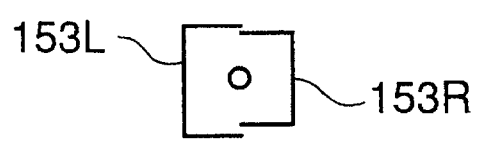

FIG. 32 shows a modification of the central visual target plates 108L, 108R in FIG. 23. This modification comprises a light source 151, a transmission type liquid crystal plate 152 capable of displaying characters, figures or the like, and character generating means 153. Computer graphics of various patterns are electronically generated on the transmission type liquid crystal plate 152 by the symbol generating means 153 and are used as central visual targets, and the transmission type liquid crystal plate 152 illuminated from behind by the light source 151 is presented to both eyes. For example, when aniseikonia examination is to be effected, figures shown in FIG. 33 may be displayed on the transmission type liquid crystal plate 152 by the character generating means 153. FIGS. 33A and 33B show central visual target marks 153L and 153R for the left eye EL and right eye ER, respectively. If the eye E to be examined is normal, then the examinee could visually perceive the visual target marks 153L and 153R as shown in FIG. 34A. If the eye E to be examined is abnormal, then the examinee will visually perceive the visual target marks 153L and 153R as shown in FIG. 34B and therefore will know the degree of aniseikonia from the difference between the sizes of the central visual targets 153L and 153R for the left eye EL and right eye ER.

To know the degree of aniseikonia, the examinee is asked to grasp, for example, response input means 155 connected to character generating means 154 shown in FIG. 35. Design is made such that when the input member 155a of the response input means 155 is inclined, the sizes of the central visual targets 153L and 153R displayed on the character generating means 154 can be varied from the direction and angle of inclination. The input member 155a of the response input means 155 is operated when the sizes of the left and right central visual targets 153L and 153R differ from each other so that the sizes of the left and right central visual targets 153L and 153R may become equal to each other to the examinee, as shown in FIG. 34A. The degree of aniseikonia can be quantitatively measured from the amount of operation of this input member 155a.

Also, when measurement of cyclophoria is to be effected, a FIG. 156 comprising a white circle and divisions as shown in FIG. 36A and a FIG. 157 comprising a white circle and a straight line as shown in FIG. 36B may be generated on the transmission type liquid crystal plate 152 by the character generating means 154 and be used as central visual targets discretely for the left eye EL and right eye ER. If the eye E to be examined is normal, then the examinee could visually confirm these central visual targets 156 and 157 as shown in FIG. 37A, but if the eye E to be examined is abnormal, then the examinee will visually confirm the central visual targets as if the straight line was inclined as shown in FIG. 37B. When the examination is to be actually effected, the examinee may be made to grasp the response input means 155 and operate the input member 155a so that the straight line may coincide with the central division, whereby the degree of cyclophoria can be quantitatively measured from the amount of this operation.

When a deep eyesight examination representing stereoscopic viewing ability is to be effected, central visual targets 158L and 158R each comprising three straight lines as shown in FIGS. 38A and 38B may be generated on the transmission type liquid crystal plate 152 by the symbol generating means 154 and be presented to the left eye EL and right eye ER, respectively. If the middle vertical bar in one of the central visual targets 158 is somewhat deviated to left or right and a parallax is given, then there will be created a sense of stereoscopic viewing. The examinee is asked to operate the response input means 155 so that the middle vertical bar in the central visual target 158 may be deviated little by little so as to provide the same depths, and the stereoscopic viewing ability can be measured by how accurately the central visual targets can be adjusted.

When heterophoria examination is to be effected, the figure at the center of the screen of the TV monitor 132 shown in FIG. 29 may be generated as the central visual target on the transmission type liquid crystal plate 152 and be presented to the left eye EL and right eye ER. As the response input means, heterophoria measuring input means 159 as shown in FIG. 39 is connected to the symbol generating means 154. If the eye to be examined is normal, then the central visual target will be image-fused into a symmetrical cross, but if the eye to be examined is abnormal, then the cross will be deformed asymmetrically.

When heterophoria measuring input means 159 in FIG. 39 is operated, the two prisms 122 of the rotatable prisms 118L and 118R shown in FIG. 23 are rotated. The vertical bar in the central visual target is moved to the left and right by an input member 155a, and the horizontal bar in the central visual target is vertically moved by an input member 155a. The examiner or the examinee operates heterophoria measuring input means 159 so that the central visual targets 153L and 153R presented to the left eye EL and right eye ER can be visually confirmed as symmetrical crosses, and the heterophoria can be quantitatively calculated from the prism angles of the rotatable prisms 118L and 118R.

FIG. 40 shows the construction of a fifth embodiment of the present invention. As shown, there are disposed visual target optical systems 161L and 161R for the left eye EL and right eye ER which comprise the same members as in the fourth embodiment shown in FIG. 23, and on the optical path between the visual target optical systems 161L and 161R, there is provided a changeover mirror 163 rotated by a step motor 162, and in the direction of reflection of the changeover mirror 163, there are disposed a lens 164 and a TV camera 165 for observation.

Beams of light from the anterior eye parts of the left eye EL and right eye ER pass through the visual target optical systems 161L and 161R, respectively, are reflected by the changeover mirror 163, pass through the lens 164, are image-picked up as anterior eye part images by the TV camera 165 and are displayed on a TV monitor. The examiner effects alignment while observing the TV monitor.

The visual targets are presented to both eyes by the visual target optical systems 161L and 161R, and eye examination by both-eye viewing is effected. During short-distance viewing examination, as shown in FIG. 40, the visual target optical systems 161L and 161R are rotated in opposite directions about the optical axes to thereby reduce the eye width and vary the angles of view of the visual targets. At this time, the changeover mirror 163 is rotated by the step motor 162 so that the anterior eye part images on the TV monitor picked up by the TV camera 165 for observation may not move, and the directions of reflection of the beams of light from the anterior eye parts are adjusted.

In this embodiment, there occurs a disadvantage that a mechanism for moving the visual target optical systems 161L and 161R for the left eye EL and right eye ER becomes large-scaled, but there is a merit that even in the case of short-distance viewing examination, the correction of astigmatism can be effected by the rotatable prisms 118L and 118R shown in FIG. 23.

Figure 41:
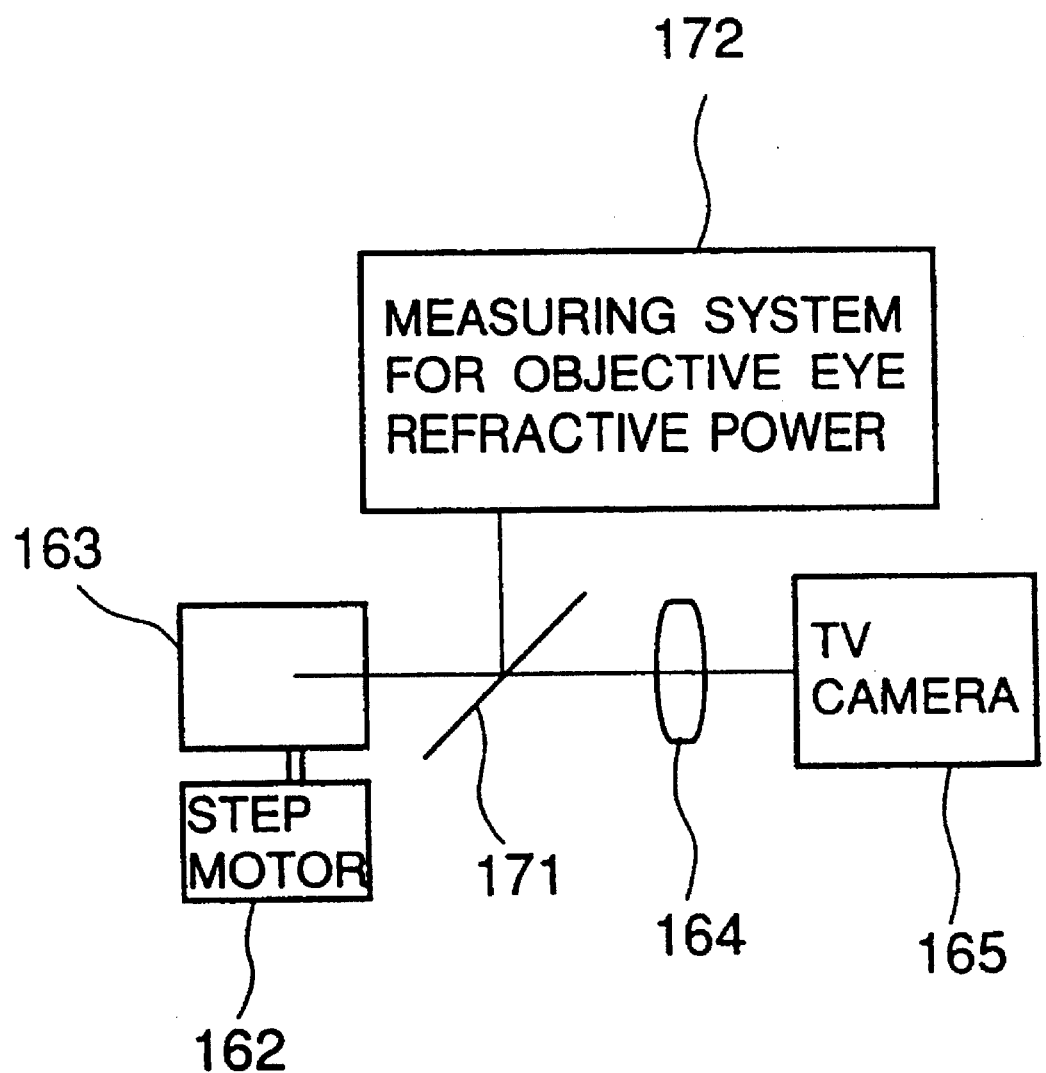
FIG. 41 shows the construction of a sixth embodiment of the present invention.

FIG. 41 shows the construction of a sixth embodiment of the present invention. As shown, a dichroic mirror 171 is inserted between the changeover mirror 163 and lens 164 of FIG. 40, and an objective refractive power measuring system 172 is disposed in the direction of reflection of the dichroic mirror 171.

A beam of light from the objective refractive power measuring system 172 is reflected by the dichroic mirror 171 and the changeover mirror 163, and is projected onto the fundus of one of the left eye EL and right eye ER. The reflected beam of light from the fundus of the eye returns along the same optical path and is received by the objective refractive power measuring system 172, and the refractive power is calculated. Subsequently, the changeover mirror 163 is rotated by the step motor 162, and the refractive power of the other eye is measured. If subjective refractive power measurement is effected by the visual target optical systems 161L and 161R, more accurate refractive power measurement could be accomplished.

What is claimed is:

1. An eye examining apparatus comprising:

a plurality of visual target projecting systems for projecting visual targets onto left and right eyes;

a visual target unit for an eye to be examined, and adapted to be projected onto the eye to be examined by one of said plurality of visual target projecting systems, said visual target unit having a first visual target mark for optometry; and a visual target for an other eye adapted to be projected onto the other eye examined by another one of said plurality of visual target projecting systems, said visual target for the other eye being provided with a second visual target mark that is the same as said first visual target mark for optometry except that the second visual target mark is non-directional, wherein said plurality of visual target projecting systems project said visual target unit and said visual target onto the left and right eyes simultaneously.

2. The apparatus according to claim 1, wherein said plurality of visual target projecting systems include a visual target projecting system for the eye to be examined, for projecting the first visual target mark onto the eye to be examined, and additional visual target projecting systems for the other eye provided on both sides of said visual target projecting system for the eye to be examined, and further include means for moving said plurality of visual target projecting systems to the left and right.

3. The apparatus according to claim 1, further comprising objective eye refraction measuring means partly sharing an optical system with one of said plurality of visual target projecting systems.

4. An eye examining apparatus comprising:

a plurality of visual target projecting systems for projecting visual targets onto left and right eyes; and a plurality of visual target units for left and right eyes, each being projected onto the left and right eyes, respectively, by said plurality of visual target projecting systems, said visual targets including a visual target having a visual target mark common to the left and right eyes and visual target marks discretely provided for the left and right eyes, wherein said plurality of visual target projecting systems simultaneously project said visual target units onto the left and right eyes.

5. The apparatus according to claim 4, further comprising eye width adjusting means for varying a spacing between said plurality of visual target projecting systems.

6. The apparatus according to claim 4, further comprising anterior eye part observation means for observing an anterior eye part of an eye to be examined from a direction of the optical axes of said visual target projecting systems.

7. The apparatus according to claim 4, wherein the visual target marks, said visual target marks common to the left and right eyes, and the visual target marks discretely provided for the left and right eyes are for optometry.

8. The apparatus according to claim 4, wherein the visual target marks common to the left and right eyes are for accommodation induction, and the visual target marks discretely provided for the left and right eyes are for eye function examination.

9. The apparatus according to claim 4, wherein said visual targets have electronic image display means for displaying visual target marks.

10. An eye examining apparatus comprising:

a plurality of visual target projecting systems provided for left and right eyes;

visual targets for the left and right eyes each being projected onto the left and right eyes, respectively, by said plurality of visual target projecting systems, each of said visual targets having a central visual target mark capable of changing the kinds of marks and a marginal visual target surrounding said central visual target mark; and diopter varying means for varying the apparent diopters of said visual targets, said diopter varying means making at least a portion of an optical member movable along an optical axis.

11. The apparatus according to claim 10, wherein each said marginal visual target is a set of stereoscopic images.

12. The apparatus according to claim 10, wherein each said central visual target presents various patterns for effecting the examination of eye functions of an eye to be examined.

13. An eye examining apparatus comprising:

a plurality of visual target projecting systems for projecting visual targets onto left and right eyes; and visual targets for the left and right eyes, each being projected onto the left and right eyes by said plurality of visual target projecting systems, a stereoscopic image being presented to an eye to be examined by projection of said visual targets, each of said visual targets having a plurality of visual target marks disposed at a distance therebetween in a direction of the optical axes of said visual target projecting systems.

* * * * *

UNITED STATES PATENT AND TRADEMARK OFFICE
CERTIFICATE OF CORRECTION

PATENT NO. : 5,483,305

DATED : January 9, 1996

INVENTOR(S) : YOSHIMI KOHAYAKAWA

Page 1 of 2

It is certified that error appears in the above-indentified patent and that said Letters Patent is hereby corrected as shown below:

ON THE COVER PAGE --

[57] ABSTRACT

Line 12, "optometry" should read --optometry,--.

COLUMN 1

Line 11, "is" should be deleted.

COLUMN 2

Line 21, "a" should be deleted; and "the" (second occurrence) should read --a--.
Line 27, "an" should be deleted.

COLUMN 3

Line 51, "the" (second occurrence) should be deleted.

COLUMN 5

Line 25, "ER" should read --ER,--.

COLUMN 8

Line 19, "Good," should read --good,--.
Line 48, "and" (second occurrence) should be deleted.

UNITED STATES PATENT AND TRADEMARK OFFICE
CERTIFICATE OF CORRECTION

PATENT NO. : 5,483,305

DATED : January 9, 1996

INVENTOR(S) : YOSHIMI KOHAYAKAWA

It is certified that error appears in the above-indentified patent and that said Letters Patent is hereby corrected as shown below:

<u>COLUMN 9</u>

Line 15, "modation" should read --modation of--.

<u>COLUMN 10</u>

Line 34, "that" should read --than--.

<u>COLUMN 12</u>

Line 21, "alone" should read --along--.
   Line 39, "constructed so" should read --so constructed--.
   Line 40, "105R" should read --105R are--.

Signed and Sealed this

Thirtieth Day of July, 1996

Attest:

BRUCE LEHMAN

*Attesting Officer*     Commissioner of Patents and Trademarks